United States Patent
Koretzky et al.

(10) Patent No.: US 6,194,633 B1
(45) Date of Patent: Feb. 27, 2001

(54) NON-HUMAN ANIMAL HAVING A FUNCTIONALLY DISRUPTED SLP-76 GENE

(75) Inventors: Gary A. Koretzky, North Liberty; James L. Clements; Roger Williamson, both of Iowa City, all of IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/013,687

(22) Filed: Jan. 26, 1998

(51) Int. Cl.⁷ .......................... A01K 67/00; G01N 33/00; C12N 15/00

(52) U.S. Cl. ...................................... 800/18; 800/3; 800/8; 800/9; 800/13; 800/14; 800/21

(58) Field of Search .............................. 800/8, 9, 13, 14, 800/18; 536/23.1

(56) References Cited

FOREIGN PATENT DOCUMENTS

| | | |
|---|---|---|
| WO 91/01140 | 2/1991 | (WO) . |
| WO 91/19796 | 12/1991 | (WO) . |
| WO 92/20808 | 11/1992 | (WO) . |
| WO 93/04169 | 3/1993 | (WO) . |
| WO 93/16177 | 8/1993 | (WO) . |
| WO 93/22443 | 11/1993 | (WO) . |
| WO 94/29442 | 12/1994 | (WO) . |

OTHER PUBLICATIONS

Araki, K. et al. "Targeted Integration of DNA Using Mutant Lox Sites in Embryonic Stem Cells" *Nucleic Acids Research* 25(4):868–872 (1997).

Bradley, A. "Modifying the Mammalian Genome by Gene Targeting" *Current Opinion in Biotechnology* 2:823–829 (1991).

Capecchi, M.R. "Altering the Genome by Homologous Recombination" *Science* 244:1288–1292 (1989).

Capecchi, M. "The New Mouse Genetics: Altering the Genome by Gene Targeting," *Trends in Genetics*, 5(3):70–76 (1989).

Crespo, P. et al. "Phosphotyrosine–Dependent Activation of Rac–1 GDP/GTP Exchange by the Vav Proto–Oncogene Procuct" *Nature* 385:169–172 (1997).

Danoff, T. M., et al. "Screening for Homologous Recombination in ES Cells Using RT–PCR" *BioTechniques* 22(1):22–26 (1997).

Fang, N. et al. "Tyrosines 113, 128, and 145 of SLP–76 Are Required for Optimal Augmentation of NFAT Promoter Activity" *The Journal of Immunology* 157:3769–3773 (1996).

Hendricks–Taylor, L.R. et al. "SLP–76 Is a Substrate of the High Affinity IgE Receptor–Stimulated Protein Tyrosine Kinases in Rat Basophilic Leukemia Cells" *The Journal of Biological Chemistry* 272(2):1363–1367 (1997).

Jackman, J. K. et al. "Molecular Cloning of SLP–76, a 76–kDa Tyrosine Phosphoprotein Associated with Grb2 in T Cells" *The Journal of Biological Chemistry* 270(13):7029–7032 (1995).

Lakhlani, P.P. et al. "Substitution of a Mutant $\alpha_{2a}$–Adrenergic Receptor via "Hit and Run" Gene Targeting Reveals the Role of this Subtype in Sedative, Analgesic, and Anesthetic–Sparing Responses in vivo" *PNAS USA* 94:9950–9955 (1997).

McDevitt, M. et al. "A 'Knockdown' Mutation Created by Cis–Element Gene Targeting Reveals the Dependence of Erythroid Cell Maturation on the Level of Transcription Factor GATA–1" *PNAS USA* 94:6781–6785 (1997).

Mizuno, K. et al. "Hematopoietic Cell Phosphatase, SHP–1, Is Constitutively Associated with the SH2 Domain–Containing Leukocyte Protein, SLP–76, in B Cells" *J. Exp. Med.* 184:457–463 (1996).

Moreadith, R.W. et al. "Gene Targeting in Embryonic Stem Genes: the New Physiology and Metabolism" *J. Mol. Med.* 75:208–216 (1997).

Motto, D.G. et al. "Implication of the GRB2–Associated Phosphoprotein SLP–76 in T Cell Receptor–Mediated Interleukin 2 Production" *J Exp Med* 183:1937–1943 (1996).

Motto, D.G. et al. "In Vivo Association of Grb2 with pp116, a Substrate of the T Cell Antigen Receptor–Activated Protein Tyrosine Kinase" *The Journal of Biological Chemistry* 269(34):21608–21613 (1994).

(List continued on next page.)

*Primary Examiner*—John L. LeGuyader
*Assistant Examiner*—Michael C. Wilson
(74) *Attorney, Agent, or Firm*—Lahive & Cockfield, LLP; Elizabeth A. Hanley, Esq.; Peter C. Lauro, Esq.

(57) ABSTRACT

A nonhuman animal having somatic and germ cells in which at least one allele of an endogenous SLP-76 gene is functionally disrupted is provided. The animal may be heterozygous or, more preferably, homozygous for the SLP-76 gene disruption and is preferably a mouse. In homozygous animals, the percentage of peripheral T cells is substantially decreased compared to wildtype animals, whereas the percentage of B cells and macrophages in the periphery is substantially normal, indicating that SLP-76 disruption causes a profound block in T cell development. The animals of the invention can be used, for example, as controls to evaluate the efficacy of SLP-76 inhibitors and to identify disease conditions that can be treated with SLP-76 inhibitors. A transgenic nonhuman animal having a functionally disrupted endogenous SLP-76 gene but which has been reconstituted with an exogenous SLP-76 transgene (e.g., a human SLP-76 gene or a SLP-76 gene whose expression in targeted to a particular cell population) is also provided. An animal that has been reconstituted with a human SLP-76 gene can be used to identify agents that modulate human SLP-76 in vivo. Nucleic acid constructs for functionally disrupting an endogenous SLP-76 gene in a host cell, recombinant vectors including the nucleic acid construct, and host cells into which the nucleic acid construct has been introduced are also encompassed by the invention.

3 Claims, 3 Drawing Sheets

OTHER PUBLICATIONS

Motto, D.G. et al. "Tyrosine Phosphorylation of Grb2–Associated Proteins Correlates with Phospholipase Cγ1 Activation in T Cells" *Molecular and Cellular Biology* 16(6):2823–2829 (1996).

Musci, M.A. et al. "Molecular Cloning of SLAP–130, an SLP–76–Associated Substrate of the T Cell Antigen Receptor–Stimulated Protein Tyrosine Kinases" *The Journal of Biological Chemistry* 272(18):11674–11677 (1997).

Musci, M.A. et al. "Three Domains of SLP–76 Are Required for Its Optimal Function in a T Cell Line" *The Journal of Immunology* 159(4):1639–1647 (1997).

Onodera, H. et al. "Differential Regulation of Activation-–Induced Tyrosine Phosphorylation and Recruitment of SLP–76 to Vav by Distinct Isoforms of the CD45 Protein-–Tyrosine Phosphatase" *The Journal of Biological Chemistry* 271(36):22225–22230 (1996).

Raab, M. et al. "Regulation of Vav–SLP–76 Binding by ZAP–70 and Its Relevance to TCRζ//CD3 Induction of Interleukin–2" *Immunity* 6(2):155–164 (1997).

Robinson, A. et al. "Characterization of Grb2–Binding Proteins in Human Platelets Activated by Fc γRIIA Cross–Linking" *Blood* 88(2):522–530 (1996).

Sunden, S.L.F. et al. "Polymorphism in and Localization of the Gene LCP2 (SLP–76) to Chromosome 5q33.1–qter" *Genomics* 35:269–270 (1996).

Tuosto, L. et al. "p95$^{vav}$ Associates with Tyrosine–Phosphorylated SLP–76 in Antigen–Stimulated T Cells" *J. Exp. Med.* 184:1161–1166 (1996).

Templeton, N.S. et al. "Efficient Gene Targeting in Mouse Embryonic Stem Cells" *Gene Therapy* 4:700–709 (1997).

Wardenburg, J.B. et al. "Phosphorylation of SLP–76 by the ZAP–70 Protein–Tyrosine Kinase Is Required for T–Cell Receptor Function" *The Journal of Biological Chemistry* 271(33):19641–19644 (1996).

Westphal, C.H. and Leder, P. "Transposon–Generated 'Knock–Out' and 'Knock–In' Gene–Targeting Constructs for Use in Mice" *Current Biology* 7:R530–R533 (1997).

Wu, J. et al "Vav and SLP–76 Interact and Functionally Cooperate in IL–2 Gene Activation" *Immunity* 4:593–602 (1996).

Wu, J. et al. "The Vav Binding Site (Y315) in ZAP–70 Is Critical for Antigen Receptor–Mediated Signal Transduction" *J. Exp. Med.* 185(10):1877–1882 (1997).

Mullins and Mullins, J. Clin. Invest., vol. 98, pp. S37–S40, 1996.

Moreadith et al, J. Mol. Med., vol. 75, pp. 208–216, 1997.

Wall, Theriogenology, vol. 45, pp. 57–68, 1996.

Moens, et al. Development, vol. 119, pp. 485–499, 1993.

Capecchi, Scientific American, vol. 270, pp. 34–41, 1994.

Pivniouk et al. Cell, vol. 94, pp. 229–238, 1998.

NON-HUMAN ANIMAL HAVING A FUNCTIONALLY DISRUPTED SLP-76 GENE

BACKGROUND OF THE INVENTION

Engagement of the T cell antigen receptor (TCR) results in the activation of protein tyrosine kinases (PTK) and the subsequent tyrosine phosphorylation of numerous proteins (Howe, L. R. and Weiss, A. (1995) *Trends Biochem. Sci.* 20:59–64; see also Perlmutter, R. M. et al. (1993) *Annu. Rev. Immunol.* 11:451–499; and Chan, A. C. et al. (1994) *Annu. Rev. Immunol.* 12:555–592). Efforts to characterize substrates of the TCR induced PTK activity led to the cloning of a 76 kDa protein termed SLP-76 (for SH2-domain-containing Leukocyte Protein of 76 kDa). SLP-76 was originally identified based upon its ability to interact with the protein Grb2, an adaptor molecule involved in coupling signal transduction pathways (Motto, D. et al. (1994) *J. Biol. Chem.* 269:21608–21613; Reif, K. et al. (1994) *J. Biol. Chem.* 269:14081–14087; Buday, L. et al. (1994) *J. Biol. Chem.* 269:9019–9023; and Sieh, M. et al. (1994) *Mol. Cell. Biol.* 14:4435–4442).

Molecular cloning of SLP-76 cDNAs (human and mouse) revealed that the SLP-76 protein comprises an acidic amino-terminal region, a proline-rich central region and a carboxy-terminal SH2 domain (Jackman J. K. et al. (1995) *J. Biol. Chem.* 270:7029–7032). Northern analysis demonstrated that SLP-76 mRNA is expressed exclusively in peripheral blood leukocytes, spleen and thymus (Jackman, J. K et al. (1995) supra). Insight into the function of SLP-76 in T cells came from experiments showing that overexpression of SLP-76 augments TCR-mediated signals that lead to the induction of IL-2 gene promoter activity (Motto, D. G. et al. (1996) *J. Exp. Med.* 183:1937–1943; Wu, J. et al. (1996) *Immunity* 4:593–602). Interestingly, three distinct regions of SLP-76 that are responsible for protein-protein interactions in T cells are required for the augmentation of IL-2 promoter activity by overexpression of SLP-76 (Fang, N. et al. (1996) *J. Immunol.* 157:3769–3773; Wardenburg, J. B. et al. (1996) *J. Biol. Chem.* 271:19641–19644; Musci, M. A. et al. (1997) *J. Immunol.* 159:1639–1647). These data suggest that SLP-76 functions as a link between proteins that regulate signals generated by TCR ligation.

Certain SLP-76-associated proteins that are thought to participate with SLP-76 in transducing signals from the TCR to the nucleus have been identified. Examples include the protooncogene Vav, which associates with the amino-terminal acidic region of SLP-76 in a phosphotyrosine dependent manner (Wu, J. et al. (1996) *Immunity* 4:593–602; Onodera, H. et al. (1996) *J. Biol. Chem.* 271:22225–22230; Tuosto, L. et al. (1996) *J. Exp. Med.* 184:1161–1167) and SLAP-130, a 130 kDa phosphoprotein that associates with the SH2 domain of SLP-76 and may act as a negative regulator of signal transduction (Musci, M. A. et al. (1997) *J. Biol. Chem.* 272:11674–11677). However, the precise role of SLP-76 in cells of the hematopoietic lineage is unclear. Accordingly, model systems in which to assess the role of SLP-76 in hematopoietic developments, as well as the involvement of SLP-76 in disease states are needed.

SUMMARY OF THE INVENTION

This invention pertains to a nonhuman animal having somatic and germ cells in which at least one allele, and preferably both alleles, of an endogenous SLP-76 gene contains exogenous DNA that has been inserted into the endogenous SLP-76 gene such that expression of the endogenous SLP-76 gene is functionally disrupted. Accordingly, the invention provides viable animals having a mutated SLP-76 gene, and thus lacking SLP-76 activity. In a preferred embodiment, the exogenous DNA that is inserted into the SLP-76 allele comprises a selectable marker gene (such as a neomycin phosphotransferase gene).

Characterization of the phenotype of the SLP-76 deficient animals of the invention revealed that functional disruption of the SLP-76 gene results in a block in T cell development such that SLP-76 deficient animals are severely lacking in peripheral T cells. In contrast, B cell and macrophage development is not substantially affected, if at all, by functional disruption of the SLP-76 gene. Thus, the animals of the invention are characterized by:

(a) a substantially decreased percentage of mature T cells in peripheral blood as compared to a non-mutant animal of the same species;

(b) a substantially normal percentage of mature B cells in peripheral blood as compared to a non-mutant animal of the same species; and (c) a substantially normal percentage of macrophages in peripheral blood as compared to a non-mutant animal of the same species.

In the nonhuman animal of the invention, the SLP-76 gene preferably is disrupted by homologous recombination between the endogenous allele and a mutant SLP-76 gene, or portion thereof, that has been introduced into an embryonic stem cell precursor of the animal. The embryonic stem cell precursor is then allowed to develop (i.e., by microinjection into a blastocyst and implantation of the blastocyst into a pseudopregnant foster animal), resulting in an animal having a functionally disrupted SLP-76 gene. The animal may have one SLP-76 gene allele functionally disrupted (i.e., the animal may be heterozygous for the mutation), or more preferably, the animal has both SLP-76 gene alleles functionally disrupted (i.e., the animal can be homozygous for the mutation). In one embodiment of the invention, functional disruption of both SLP-76 gene alleles produces animals in which expression of the SLP-76 gene product in cells of the animal is substantially reduced or substantially absent relative to non-mutant animals. In another embodiment, the SLP-76 gene alleles can be disrupted such that an altered (i.e., mutant) SLP-76 gene product is produced in cells of the animal. A preferred nonhuman animal of the invention having a functionally disrupted SLP-76 gene is a mouse.

The animals of the invention are useful, for example, as animal models of T cell immunodeficiency, as an in vivo system to evaluate the role of SLP-76 in various biological processes (e.g., T cell development, B cell development, macrophage development, platelet function, and the like), and as standard controls by which to evaluate the efficacy and side effects of putative SLP-76 inhibitors. The animals also can also be used to identify disease states for treatment with SLP-76 inhibitors. For example, the invention provides a method for identifying a disease condition treatable with a SLP-76 inhibitor which involves attempting to induce the disease condition in the animal of invention and determining the susceptibility or resistance of the animal to the disease condition. Resistance of the SLP-76 deficient animal to the disease condition, relative to a nonmutant animal of the same species, is indicative that the disease condition is treatable with a SLP-76 inhibitor. One can attempt to induce the disease condition in the animal by, for example, administering to the animal a stimulus that induces the disease condition in a nonmutant animal of the same species or by breeding the SLP-76 deficient animal with a second animal that is susceptible to the disease condition.

Another aspect of the invention pertains to a nonhuman animal having a functionally disrupted endogenous SLP-76 gene but which also carries in its genome, and expresses, a SLP-76 transgene randomly integrated into the genome of the animal. In one embodiment, the transgene encodes a SLP-76 protein from the same species as the animal (e.g., a SLP-76 deficient mouse can be reconstituted with a mouse SLP-76 transgene), although expression of the transgene can be directed to a particular cell population. In another embodiment, the SLP-76 transgene encodes a heterologous SLP-76 protein (i.e., a SLP-76 protein from another species). Preferably, the animal is a mouse and the heterologous SLP-76 is a human SLP-76. An animal of the invention which has been reconstituted with human SLP-76 can be used to identify agents that inhibit human SLP-76 in vivo. For example, an agent to be tested can be administered to such an animal and the activity of human SLP-76 in the animal can be measured. Decreased human SLP-76 activity in the animal in the presence of the agent, as compared to human SLP-76 activity in the animal in the absence of the agent, is indicative that the agent inhibits human SLP-76 in vivo.

Yet another aspect of the invention pertains to a nucleic acid construct for functionally disrupting an SLP-76 gene in a host cell. The nucleic acid construct comprises: a) a nonhomologous replacement portion; b) a first homology region located upstream of the nonhomologous replacement portion, the first homology region having a nucleotide sequence with substantial identity to a first SLP-76 gene sequence; and c) a second homology region located downstream of the nonhomologous replacement portion, the second homology region having a nucleotide sequence with substantial identity to a second SLP-76 gene sequence, the second SLP-76 gene sequence having a location downstream of the first SLP-76 gene sequence in a naturally occurring endogenous SLP-76 gene. Additionally, the first and second homology regions are of sufficient length for homologous recombination between the nucleic acid construct and an endogenous SLP-76 gene in a host cell when the nucleic acid molecule is introduced into the host cell.

In a preferred embodiment, the nonhomologous replacement portion comprises a positive selection expression cassette, preferably including a neomycin phosphotransferase gene operatively linked to a regulatory element(s). In another preferred embodiment, the nucleic acid construct also includes a negative selection expression cassette distal to either the upstream or downstream homology regions. A preferred negative selection cassette includes a herpes simplex virus thymidine kinase gene operatively linked to a regulatory element(s).

Another aspect of the invention pertains to recombinant vectors into which the nucleic acid construct of the invention has been incorporated. Yet another aspect of the invention pertains to host cells into which the nucleic acid construct of the invention has been introduced to thereby allow homologous recombination between the nucleic acid construct and an endogenous SLP-76 gene of the host cell, resulting in functional disruption of the endogenous SLP-76 gene. The host cell can be a mammalian cell that normally expresses SLP-76, such as a human T cell, thymocyte, macrophage or NK cell, or a pluripotent cell, such as a mouse embryonic stem cell. Further development of an embryonic stem cell into which the nucleic acid construct has been introduced and homologously recombined with the endogenous SLP-76 gene produces a transgenic nonhuman animal having cells that are descendant from the embryonic stem cell and thus carry the SLP-76 gene disruption in their genome. Animals that carry the SLP-76 gene disruption in their germline can then be selected and bred to produce animals having the SLP-76 gene disruption in all somatic and germ cells. Such mice can then be bred to homozygosity for the SLP-76 gene disruption.

DETAILED DESCRIPTION OF THE INVENTION

Figure 1:
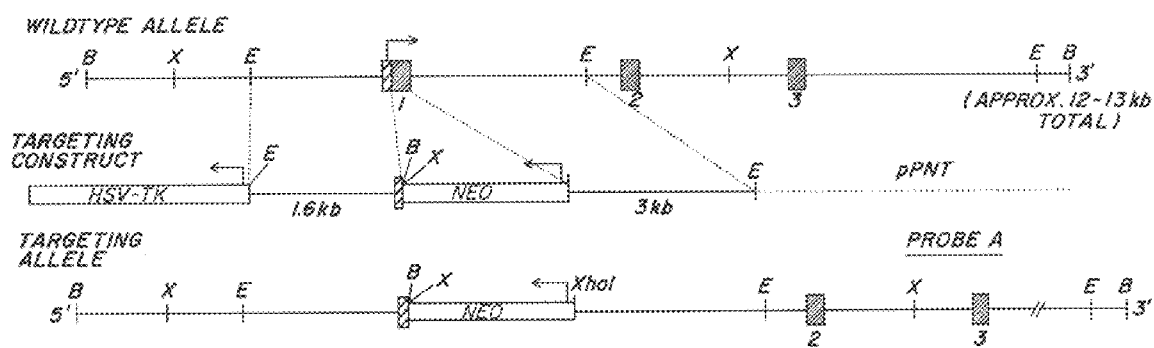
FIG. 1A is a schematic representation of the structure of the wildtype murine SLP-76 allele (showing BamHI (B), EcoRI (E) and XbaI (X) restriction sites), a targeting construct for homologous recombination and the targeted SLP-76 allele following homologous recombination.
FIG. 1B is a photograph of a Southern blot depicting genomic DNA from a homozygous SLP-76 deficient mouse (lane 1), genomic DNA from wild type mice (lanes 2 and 3) and genomic DNA from a heterozygous SLP-76 deficient mice (lanes 4 and 5).

One aspect of the invention pertains to a nonhuman animal having cells in which at least one allele of an endogenous SLP-76 gene is functionally disrupted. Preferably, both the somatic and germ cells of the animal have an SLP-76 gene allele functionally disrupted. Even more preferably, the somatic and germ cells have both alleles of the SLP-76 gene functionally disrupted. Thus, the invention provides nonhuman animals in which SLP-76 activity is defective. As demonstrated in Example 3, a homozygous SLP-76 deficient animal of the invention (i.e., an animal in which both SLP-76 alleles are disrupted) is characterized by a phenotype in which the percentage of mature T cells in the periphery (e.g., peripheral blood and spleen) is substantially decreased, as compared to a heterozygous SLP-76 deficient animal (i.e., an animal in which one SLP-76 allele is disrupted) or a wildtype animal (i.e., an animal in which neither SLP-76 allele is disrupted). The phenotype of a homozygous SLP-76 deficient animal of the invention is further characterized by an essentially normal percentage of mature B cells and macrophages in the periphery (e.g., peripheral blood and spleen), as compared to a heterozygous SLP-76 deficient animal or a wildtype animal.

The phenotype of the SLP-76 deficient animals of the invention is surprising for a number of reasons. First, SLP-76 has been shown to interact with a number of proteins in T cells (e.g., Grb2, Vav, SLAP-130) and these proteins with which SLP-76 interacts have also been shown to associate with a number of other proteins, suggesting that there could be redundancy in the role that SLP-76 plays in T cells. Thus, it was unexpected that mutation of SLP-76 would have such a marked and drastic effect on T cell development. Furthermore, considering that SLP-76 was known to be expressed at significant levels in the macrophage/monocyte lineage, it was unexpected that macrophage development would be essentially normal in the SLP-76 deficient mice.

As used herein, a SLP-76 gene that is "functionally disrupted" has a mutation that prevents the normal function of the SLP-76 gene, e.g., prevents expression of a normal SLP-76 gene product or prevents expression of normal amounts of the SLP-76 gene product. The mutation causing the functional disruption can be an insertion, deletion or point mutation(s). In one embodiment, both SLP-76 gene alleles are functionally disrupted such that expression of the SLP-76 gene product is substantially reduced or substantially absent in cells of the animal. The term "substantially reduced" is intended to mean that less than 50% of the normal amount of SLP-76 protein is produced in cells of the animal. The term "substantially absent" is intended to mean that essentially undetectable amounts of SLP-76 gene product are produced in cells of the animal. A mutation in which SLP-76 protein expression is substantially absent is also referred to in the art as a "null mutation" and an animal carrying such a null mutation is also referred to as a "knockout animal." Although animals with substantially reduced or substantially absent levels of SLP-76 protein are typically made by disrupting the coding region of the SLP-76 gene, an alternative approach is to disrupt the cis-regulatory element(s) of the gene such that transcription of the gene is downmodulated. Such an approach, referred to as a "knockdown" mutation, is described further in McDevitt, M. A. et al. (1997) *Proc. Natl. Acad. Sci. USA* 94:6781–6785.

In another embodiment, both SLP-76 gene alleles are functionally disrupted such that an altered form of the SLP-76 gene product is expressed in cells of the animal. For example, one or more point mutations or deletion mutations can be introduced into the SLP-76 gene to thereby alter the amino acid sequence of the SLP-76 gene product encoded therein. In vitro structure/function experiments have shown that three distinct regions of SLP-76, namely the acidic amino-terminal region, the proline-rich central region or the carboxy-terminal SH2 domain, are necessary for SLP-76 augmentation of IL-2 promoter activity (see Musci, M. A. et al. (1997) *J. Immunol.* 159:1639–1647; Fang, N. et al. (1996) *J. Immunol.* 157:3769–3773; Wardenburg, J. B. et al. (1996) *J. Biol. Chem.* 271:19641–19644). For example, mutation of tyrosines 113, 128 and/or 145 of SLP-76 affects its activity (Fang, N. et al. (1996) *J. Immunol.* 157:3769–3773). Accordingly, a "functionally disrupted" SLP-76 gene of the invention can be one which is still capable of expressing a SLP-76 gene product at essentially normal levels but which expresses a mutant form of SLP-76 (e.g., a form mutated within the acidic amino-terminal region, the proline-rich central region or the carboxy-terminal SH2 domain).

In the animals of the invention, at least one allele of an endogenous SLP-76 gene contains exogenous DNA that has been inserted into the endogenous SLP-76 gene such that expression of the endogenous SLP-76 gene is functionally disrupted. As used herein, the term "exogenous DNA" is intended to refer to DNA that is not found within the endogenous SLP-76 gene in the genome of the animal as it exists in nature. That is, exogenous DNA represents "transgenic" DNA that has been specifically introduced into the genome of the animal by genetic manipulation. In a preferred embodiment, the exogenous DNA inserted into the endogenous SLP-76 gene comprises a selectable marker (e.g., a neomycin phosphotransferase gene), which aids in identifying cells that have exogenous DNA specifically inserted into the SLP-76 gene.

As used herein, an animal that is characterized by a "substantially decreased" percentage of mature T cells in its periphery (e.g., peripheral blood or spleen) is intended to refer to an animal that has less than half the normal number of mature T cells in its periphery, as compared to a non-mutant animal of the same species. In embodiments of the invention in which SLP-76 gene expression is substantially absent in the animal (i.e., homozygous SLP-76 deficient animals), the decrease in the percentage of mature T cells in the periphery is even more marked (see Example 3 and FIG. 2). As used herein, an animal characterized by a "substantially normal" percentage of mature B cells and/or macrophages in its periphery (e.g., peripheral blood or spleen) is intended to refer to an animal that has about 90%, or greater, of the amount of mature B cells and/or macrophages as compared to a non-mutant animal of the same species. In embodiments of the invention in which SLP-76 gene expression is substantially absent in the animal (i.e., homozygous SLP-76 deficient animals), the percentage of mature B cells and macrophages in the periphery is essentially normal (see Example 3 and FIG. 2).

The SLP-76 deficient animals of the invention are characterized by additional features that evidence a severe block in T cell development. For example, the thymus of a homozygous deficient animal yields approximately 100-fold fewer thymocytes compared to heterozygous and wildtype littermates. Additionally, the thymocytes of the homozygous deficient animals are substantially reduced in the numbers of CD4+, CD8+, CD4+ CD8+ and CD3+ cells, and substantially increased in the numbers of CD25+ cells (see Example 3 and FIG. 3).

In a preferred embodiment, a SLP-76 gene allele is functionally disrupted in a cell by homologous recombination between the allele and a targeting vector comprising a mutant SLP-76 gene, or portion thereof, that is introduced into the cell. The cell can be a differentiated cell type that normally expresses SLP-76, such as a T cell, thymocyte, macrophage/monocyte, or NK cell. Alternatively, the cell can be a pluripotent progenitor cell that can develop into an animal, such as an embryonic stem cell. When the cell is an embryonic stem cell, the cell can be introduced into a blastocyst and the blastocyst allowed to develop in a foster animal to thereby produce an animal having somatic and germ cells in which an SLP-76 gene allele is functionally disrupted. Such an animal is referred to herein as a "homologous recombinant" animal. A preferred homologous recombinant animal of the invention is a mouse.

To create a homologous recombinant cell or animal, a targeting vector is prepared which contains DNA encoding an SLP-76 gene, or portion thereof, having a mutation introduced therein. A preferred targeting vector for creating a null mutation in an endogenous SLP-76 gene includes SLP-76-encoding DNA into which has been inserted non-SLP-76 encoding DNA. For example, in one embodiment, a targeting vector of the invention for functionally disrupting an endogenous SLP-76 gene in a cell comprises:

a) a nonhomologous replacement portion;

b) a first homology region located upstream of the nonhomologous replacement portion, the first homology region having a nucleotide sequence with substantial identity to a first SLP-76 gene sequence; and c) a second homology region located downstream of the nonhomologous replacement portion, the second homology region having a nucleotide sequence with substantial identity to a second SLP-76 gene sequence, the second SLP-76 gene sequence having a location downstream of the first SLP-76 gene sequence in a naturally occurring endogenous SLP-76 gene.

Thus, the nonhomologous replacement portion is flanked 5' and 3' by nucleotide sequences with substantial identity to SLP-76 gene sequences. A nucleotide sequence with "substantial identity" to an SLP-76 gene sequence is intended to describe a nucleotide sequence having sufficient homology to an SLP-76 gene sequence to allow for homologous recombination between the nucleotide sequence and an endogenous SLP-76 gene sequence in a host cell. Typically, the nucleotide sequences of the flanking homology regions are at least 90%, more preferably at least 95%, even more preferably at least 98% and most preferably 100% identical to the nucleotide sequences of the endogenous SLP-76 gene to be targeted for homologous recombination. Most preferably, the flanking homology regions are isogenic with the targeted endogenous allele (e.g., the DNA of the flanking regions is isolated from cells of the same genetic background as the cell into which the targeting construct is to be introduced). Additionally, the flanking homology regions of the targeting vector are of sufficient length for homologous recombination between the targeting vector and an endogenous SLP-76 gene in a host cell when the vector is introduced into the host cell. Typically, the flanking homology regions are at least 1 kilobase in length and more preferably are least several kilobases in length.

A typical targeting vector has a positive selection expression cassette as the nonhomologous replacement portion. The term "positive selection expression cassette" refers to nucleotide sequences encoding a positive selection marker operatively linked to regulatory elements that control expression of the positive selection marker (e.g., promoter and polyadenylation sequences). A "positive selection marker" allows for selection of cells which contain the marker, whereas cells that do not contain and express the marker are selected against (e.g., are killed by the selecting agent). For example, a preferred positive selection expression cassette includes a neomycin phosphotransferase ("neo") gene operatively linked to a promoter and a polyadenylation signal. Cells carrying and expressing the neo gene exhibit resistance to the selecting agent G418.

In addition to the positive selection expression cassette, a targeting vector of the invention typically also includes a negative selection expression cassette located distal to either the upstream or downstream homology regions (i.e., the regions substantially identical to SLP-76-encoding sequences). A "negative selection expression cassette" refers to nucleotide sequences encoding a negative selection marker operatively linked to regulatory elements that control expression of the negative selection marker. A "negative selection marker" allows for selection against cells which carry the marker, e.g., cells that contain and express the marker are killed by a selecting agent, whereas cells that do not contain and express the negative selection marker survive. For example, a preferred negative selection expression cassette includes a herpes simplex virus thymidine kinase ("tk") gene operatively linked to a promoter and a polyadenylation signal. Cells that contain and express the tk gene can be killed, for example, by the selecting agent gancyclovir.

This configuration of the targeting vector allows for use of the "positive/negative" selection technique for selecting homologous recombinants: cells into which the targeting vector has been introduced are selected that contain and express the positive selection marker but which have lost the negative selection marker. Accordingly, these cells carry the nonhomologous replacement portion DNA (e.g., the inserted neo gene) but have lost the DNA encoding the negative selection marker located distal thereto in the targeting vector, likely as a result of homologous recombination between the targeting vector and the endogenous SLP-76 gene.

In a preferred embodiment, the targeting vector includes flanking homologous regions having substantial identity to mouse SLP-76 gene sequences to thereby target an endogenous mouse SLP-76 gene in a mouse host cell (e.g., a murine embryonic stem cell) for homologous recombination. Murine SLP-76 genomic DNA used as the flanking homology regions of the targeting vector can be isolated from a murine genomic DNA library by screening the library with a cDNA probe encompassing all or part of the murine SLP-76 cDNA using standard techniques. For example, a λFIXII genomic library (available commercially from Stratagene) can be screened with a probe from the mouse SLP-76 cDNA to isolate mouse SLP-76 genomic DNA for use in a targeting vector (see Example 1). Cloning of the mouse SLP-76 cDNAs is described in detail in Jackman J. K. et al. (1995) *J. Biol. Chem.* 270:7029–7032 and the nucleotide sequence of the mouse SLP-76 cDNA is available in the GenBank database at accession number MMU20159. Localization of the SLP-76 gene to chromosome 5q33.1-qter is described in Sunden, S. L. F. et al. (1996) *Genomics* 35:269–270.

A restriction map of 12–13 kb of the mouse SLP-76 gene is shown in FIG. 1A. To create a targeting vector for functionally disrupting an endogenous mouse SLP-76 gene, the nonhomologous replacement portion (e.g., a positive selection expression cassette, such as the neo gene) preferably is inserted immediately downstream of the translational start site of the mouse SLP-76 gene in the targeting vector. The nonhomologous replacement portion preferably is flanked upstream by approximately 1.6 kb of adjacent SLP-76 gene sequence and downstream by approximately 3 kb of adjacent SLP-76 gene sequence (see FIG. 1A for a schematic diagram of a preferred targeting construct). However, it will be appreciated by the skilled artisan that a nonhomologous replacement portion can be inserted at other locations within the SLP-76 gene, and flanked by different homology regions, to thereby functionally disrupt the gene. Construction of a targeting vector for functional disruption of a mouse SLP-76 gene is described in further detail in Example 1. The functional disruption of the mouse SLP-76 gene sequence may prevent expression of a full-length mouse SLP-76 mRNA transcript (e.g., by insertion of the neo gene) or may lead to expression of an mouse SLP-76 mRNA transcript that encodes an altered form of mouse SLP-76.

Alternatively, to target a human SLP-76 gene in a human host cell (e.g., a T cell, thymocyte, macrophage/monocyte or NK cell) for homologous recombination, the targeting vector includes flanking homology regions having substantial identity to human SLP-76 gene sequences. Human SLP-76 genomic DNA sequences can be isolated by screening a human genomic DNA library with a cDNA probe encompassing all or part of the human SLP-76 cDNA using standard techniques. Cloning of the human SLP-76 cDNAs is described in detail in Jackman J. K. et al. (1995) *J. Biol. Chem.* 270:7029–7032 and the nucleotide sequence of the human SLP-76 cDNA is available in the GenBank database at accession number HSU20158. As described for the mouse SLP-76 gene, the functional disruption of the human SLP-76 gene sequence in a human cell may prevent expression of a full-length human SLP-76 mRNA transcript or may lead to expression of an human SLP-76 mRNA transcript that encodes an altered form of human SLP-76.

To functionally disrupt an endogenous SLP-76 gene allele in a host cell, a targeting vector of the invention is introduced into the host cell, e.g., a differentiated cell that normally expresses SLP-76 or an embryonic stem cell, and homologous recombinants are selected. A targeting vector can be introduced into a host cell by any of several techniques known in the art suitable for the introduction of exogenous DNA (e.g., calcium phosphate precipitation, DEAE-dextran transfection, microinjection, lipofection and the like) but is most preferably introduced into the host cell by electroporation. After introduction of the vector into the host cell, the cell is cultured for a period of time and under conditions sufficient to allow for homologous recombination between the introduced targeting vector and an endogenous SLP-76 gene. Host cells are selected (e.g., by the positive/negative selection techniques described above) and screened for homologous recombination at the endogenous SLP-76 gene locus by standard techniques (e.g., Southern hybridizations using a probe which distinguishes the normal endogenous allele from the homologous recombinant allele).

To create a cell homozygous for the SLP-76 gene disruption, the G418 escalation method of Mortensen, R. N. et al. ((1992) *Mol. Cell. Biol.* 12:2391–2395) can be used on the heterozygous cells. Alternatively, the first allele of a wild type host cell can be disrupted by a first homologous recombination event that is selected with one marker (e.g., G418 resistance) and then the second allele of the heterozygous cells can be disrupted by a second homologous recombination event that is selected with a different marker (e.g., hygromycin resistance) (see e.g., TERiele, H. (1990) *Nature* 348:649–651).

To create a homologous recombinant animal of the invention, an embryonic stem cell having one SLP-76 gene allele functionally disrupted is introduced into a blastocyst, the blastocyst is implanted into a pseudopregnant foster mother, and the embryo allowed to develop to term. The resultant animal is a chimera having cells descendant from the embryonic stem cell. Chimeric animals in which the embryonic stem cell has contributed to the germ cells of the animal can be mated with wild type animals to thereby produce animals heterozygous for the SLP-76 gene disruption in all somatic and germ cells. The heterozygous animals can then be mated to create animals homozygous for the SLP-76 gene disruption (i.e., having both SLP-76 gene alleles functionally disrupted). These animals can be used as control or test animals for in vivo assays (described in further detail below). Additionally, cells of the animal homozygous for the SLP-76 gene disruption can be isolated from the animals and cultured for use in in vitro assays. Furthermore, immortalized cell lines can be prepared from cells of the animal using standard techniques for cell immortalization, e.g., by transfection of the cells with an expression vector encoding myc, ras or SV40 large T antigen.

Targeting vectors and methodologies for functionally disrupting a murine SLP-76 gene by homologous recombination are described in further detail in Examples 1–2. Moreover, in addition to the foregoing and the Examples, other methods and reagents known in the art for specifically altering an endogenous gene in a host cell can be applied to the SLP-76 gene to create cells and animals of the invention. For a general review on gene targeting in embryonic stem cells see Moreadith and Radford (1997) *J. Mol. Med.* 75:208–216. For additional descriptions of targeting vectors and methodologies, see also e.g., Thomas, K. R. et al. (1986) *Cell* 44:419–428; Thomas, K. R. et al. (1987) *Cell* 51:503–512; Thomas, K. R. et al. (1992) *Mol. Cell. Biol.* 12:2919–2923; Deng, C. and Capecchi, M. R. (1992) *Mol. Cell. Biol.* 12:3365–3371; Hasty, P. et al. (1992) *Mol. Cell. Biol.* 12:2464–2474; Li, E. et al. (1992) *Cell* 69:915; Zhang, H., et al. (1994) *Mol. Cell. Biol.* 14:2404–2410; Bradley, A. in *Teratocarcinomas and Embryonic Stem Cells: A Practical Approach,* E. J. Robertson, ed. (IRL, Oxford, 1987) pp. 113–152; PCT International Publication No. WO 90/11354; PCT International Publication No. WO 91/01140; PCT International Publication No. WO 91/19796; PCT International Publication No. WO 92/20808; and PCT International Publication No. WO 93/04169. Both copies of an SLP-76 gene can be functionally disrupted according to the methods described in PCT International Publication WO 93/16177.

Alternative approaches to the positive/negative selection method of homologous recombination described above are available in the art, such as "hit and run" gene targeting (see e.g., Lakhlani, P. P. et al. (1997) *Proc. Natl. Acad. Sci. USA* 94:9950–9955) and transposon-generated "knock-out" and "knock-in" gene targeting (see e.g., Westphal and Leder (1997) *Curr. Biol.* 7:530–533). Methods for efficient gene targeting, allowing for a high frequency of homologous recombination events, are described in Templeton, N. S. et al. (1997) *Gene Ther.* 4:700–709. This type of efficient gene targeting can allow for detection of homologous recombination events without the need for the use of selectable markers. Moreover, efficient methods for screening for homologous recombination in ES cells using reverse transcription-polymerase chain reaction (RT-PCR) have been described (see Danoff, T. M. et al. (1997) *Biotechniques* 22:22–24, 26.

Additionally, recombinase-mediated homologous recombination can be used to functionally disrupt an SLP-76 gene (see e.g., PCT International Publication WO 93/22443). Numerous examples of the use of the Cre/Lox recombinase system of bacteriophage for precise genomic manipulation are known in the art (see e.g., Gagneten, S. et al. (1997) *Nucl. Acids Res.* 25:3326–3331; Xiao and Weaver (1997) *Nucl. Acids Res.* 25:2985–2991; Agah, R. et al. (1997) *J. Clin. Invest.* 100:169–179; Barlow, C. et al. (1997) *Nucl. Acids Res.* 25:2543–2545; Araki, K. et al. (1997) *Nucl. Acids Res.* 25:868–872). One advantage of the Cre/Lox system is that it can allow for conditional inactivation of a gene interest. Additionally, methods and reagents for conditional inactivation of a gene of interest using a tetracycline-regulated gene expression system are described in PCT Publication WO 94/29442 and U.S. Pat. No. 5,650,298.

In addition to allowing for introduction of a null mutation in an SLP-76 gene allele, similar techniques to those discussed above can be used to introduce point mutations or deletions into an SLP-76 gene allele. For example, a point mutation(s) can be introduced into one or more of the three functional domains of SLP-76 (the amino acidic region, the central proline-rich region and/or the carboxy SH2 domain). Preferred residues to be mutated include $Tyr_{113}$, $Tyr_{128}$ and $Tyr_{145}$, which have been shown to be important for SLP-76 activity (see Fang, N. et al. (1996) *J. Immunol.* 157:3769–3773). Point or deletion mutations can be introduced into an SLP-76 gene allele by, for example, the "hit and run" homologous recombination procedure (as described in Valancius, V. and Smithies, O. (1991) *Mol. Cell. Biol.* 11:1402–1408; and Hasty, P. et al. (1991) *Nature* 350:243–246) or by the double replacement homologous recombination procedure (as described in Wu, H. et al. (1994) *Proc. Natl. Acad. Sci. USA* 91:2819–2823). Accordingly, in another embodiment, the invention provides homologous recombinant cells and animals (e.g., human cells or nonhuman animals) that express an altered SLP-76 gene product.

In another embodiment, the invention provides a nonhuman animal having a functionally disrupted endogenous SLP-76 gene and which further comprises a transgene encoding a SLP-76 protein. In one embodiment, the transgene is randomly integrated into the genome of the animal. The transgene can encode a SLP-76 protein from the same species as the animal (e.g., a mouse SLP-76 transgene in a SLP-76 knockout mouse). Such an animal can be made, for example, by mating the SLP-76 deficient animal with a second animal that carries a SLP-76 transgene in its genome. In one embodiment, the animal to which the SLP-76 deficient animal is mated carries a SLP-76 transgene whose expression is limited to a particular cell type (based upon the regulatory sequences to which the transgene is linked). For example, a SLP-76 deficient animal of the invention can be cross-bred with a SLP-76 transgenic animal which expresses SLP-76 only in thymic cells due to use of a thymic specific promoter.

Alternatively, the SLP-76 transgene can encode a heterologous SLP-76 protein (i.e., a SLP-76 protein from a different species than the animal). For example, an animal of the invention homozygous for a SLP-76 null mutation, or a cell derived therefrom, can be reconstituted with a human SLP-76 gene to create a nonhuman cell or animal that expresses a human SLP-76 gene product. These cells and animals can then be used to screen compounds to identify agents that inhibit the activity of human SLP-76, either in cultured cells or in vivo in animals (described further below). A human SLP-76 reconstituted animal can be made, for example, by introducing nucleic acid encoding human SLP-76 into the genome of embryonic progenitor cells obtained from an animal of the invention and allowing the embryonic cells to develop using standard techniques for creating transgenic and homologous recombinant animals. Nucleic acid encoding human SLP-76 can be integrated randomly into the genome of a SLP-76 deficient animal (e.g., by microinjection of a human SLP-76 gene construct into fertilized oocytes obtained from an SLP-76 deficient animal) or the nucleic acid can be integrated by homologous recombination into the endogenous SLP-76 locus (i.e., the endogenous SLP-76 gene bearing the null mutation can be replaced by an exogenously introduced human SLP-76 gene). The human SLP-76 gene construct can include upstream and/or downstream regulatory elements that allow for either tissue-specific, regulated expression of the SLP-76 polypeptide or constitutive expression of the human SLP-76 polypeptide in cells of the mammal. A human SLP-76-reconstituted animal of the invention also provides a source of nonhuman cells that express human SLP-76 polypeptide. Such cells can be isolated from the animal and, if necessary, immortalized by standard techniques.

The features and characteristics of the animals of the invention, and cells derived therefrom, make them useful for a wide variety of applications, as described in further detail in the subsections below:

Uses of the Animals and Cells of the Invention

1. In one embodiment, the animals of the invention are used as models for T cell immunodeficiency. As discussed in Example 3, the SLP-76 animals of the invention are severely impaired for T cell development, yet have minimally affected, if at all, B cell and macrophage development. Accordingly, these animals provide a model system for selective immunodeficiency in the T cell compartment.

2. The animals of the invention are generally useful to study the role of SLP-76 in various biological processes, including hematopoietic development and function, platelet function and atherosclerosis.

3. In another embodiment, the animals of the invention, or cells derived therefrom, are used as positive control animals by which to evaluate the efficacy of SLP-76 inhibitors. That is, the homozygous animals of the invention provide a standard for 100% SLP-76 inhibition. In a screening assay to identify and assess the efficacy of SLP-76 inhibitors, a wild type animal (or cells derived therefrom) not treated with the inhibitor can be used as the 0% inhibition standard, an animal heterozygous for an SLP-76 gene disruption (or cells derived therefrom) can be used as the 50% inhibition standard and an animal homozygous for an SLP-76 gene disruption (or cells derived therefrom) can be used as the 100% inhibition standard. The amount of SLP-76 activity in a subject treated with an SLP-76 inhibitor is then assessed relative to these standards.

4. The animals of the invention, or cells derived therefrom, also can be used to screen SLP-76 inhibitors for side effects or toxicity resulting from the inhibitor's action on a target(s) other than SLP-76 itself. For example, a SLP-76 inhibitor is administered to an animal of the invention homozygous for an SLP-76 null mutation and the resulting effects are monitored to evaluate side effects or toxicity of the inhibitor. Since the animal lacks the normal target of the SLP-76 inhibitor (i.e., active SLP-76 protein), an effect observed upon administration of the inhibitor to the SLP-76 null mutant can be attributed to a side effect of the SLP-76 inhibitor on another target(s) (e.g., an SLP-76 isoform). Accordingly, the animals of the invention are useful for distinguishing these side effects from the direct effects of the inhibitor on SLP-76 activity.

5. The animals of the invention can also be used in in vivo screening assays to identify diseases in which SLP-76 plays a role in the pathogenesis of the diseases. Such screening assays are further useful for identifying diseases that may be treated by SLP-76 inhibitors.

To identify a disease condition involving SLP-76, and thus potentially treatable by a SLP-76 inhibitor, an attempt is made to induce the disease condition in an animal of the invention homozygous for the SLP-76 gene disruption. In one embodiment, the attempt to induce the disease condition involves administering a stimulus to the animal that induces the disease condition in a wild-type animal. In another embodiment, the attempt to induce the disease condition involves breeding an animal of the invention with another animal genetically prone to a particular disease. The animals are crossbred at least until they are homozygous for the SLP-76 null mutation.

For example, an animal of the invention can be bred with an animal prone to a particular autoimmune disease to assess the involvement of SLP-76 in the pathology of the autoimmune disease and to determine whether an SLP-76 inhibitor may be effective in treating the autoimmune disease. Examples of mice strains genetically susceptible to particular autoimmune diseases include the MRL/lpr mouse (Cohen, P. L. et al. (1991) *Ann. Rev. Immunol.* 9:243–269), which is a model for lupus erythematosus, and the NOD mouse (Rossinni, A. A. (1985) *Ann. Rev. Immunol.* 3:289–320), which is a model for insulin-dependent diabetes mellitus. Non-limiting examples of other mouse strains (and their disease susceptibilities) which can be bred with the animals of the invention include: DBA/1 (collagen-induced arthritis; model for rheumatoid arthritis)(Wooley, P. H. et al. (1981) *J. Exp. Med.* 154:688–700), BALB/c (proteoglycan-induced arthritis and spondylitis; model for rheumatoid arthritis and ankylosing spondylitis)(Glant, T. T. et al. (1987) *Arthritis Rheum.* 30:201–212), PL/J (experimental autoimmune encephalomyelitis; model for multiple sclerosis)

(Fritz, R. B. et al. (1983) *J. Immunol.* 130:191–194), NZB/KN (polyarthritis; model for rheumatoid arthritis and osteoarthritis)(Nakamura, K. et al. (1991) *Arthritis Rheum.* 34:171–179), C57BL (osteoarthritis; Pataki, A. et al. (1990) *Agents Actions* 29:201–209), STR/ORT (polyarthritis; model for rheumatoid arthritis and osteoarthritis)(Dunham, J. et al. (1990) *J. Orthop. Res.* 8:101–104), and Tsk/+ (systemic sclerosis; Siracusa, L. D. et al. (1993) *Genomics* 17:748–751). For MHC-associated disease models, offspring of the crossbreeding are selected that maintain the disease-susceptible MHC haplotype. Many mouse strains genetically susceptible to particular diseases are available from The Jackson Laboratory, Bar Harbor, Me. or other commercial or academic sources. The disease condition is then induced in the crossbred animals either spontaneously or experimentally.

Following induction of the disease condition in the SLP-76 null mutant animal, the susceptibility or resistance of the animal to the disease condition is determined. Resistance of the animal to the disease condition, relative to a wild-type control animal, is indicative that the pathology of the disease condition may involve SLP-76 and thus that the disease condition may be treatable with an SLP-76 inhibitor.

For the foregoing disease models, it may be preferable to use a SLP-76 deficient animal in which the SLP-76 deficiency can be induced in a conditional manner (e.g., by Cre/Lox recombination or by tetracycline-regulated conditional knockout, as described above), to more accurately approximate the effect of administering a SLP-76 inhibitor to a patient suffering from the disease whose immune system has developed in the presence of SLP-76.

6. In another embodiment, an animal of the invention homozygous for an SLP-76 null mutation, or a cell derived therefrom, is reconstituted with a human SLP-76 gene to create a nonhuman cell or animal that expresses a human SLP-76 gene product (described above). These cells and animals can then be used to screen compounds to identify agents that inhibit the activity of human SLP-76, either in cultured cells or in vivo in animals. For example, a panel of compounds can be administered individually to the animal and the level of human SLP-76 activity in the animal can be measured. Decreased human SLP-76 activity in the animal in the presence of an agent, as compared to human SLP-76 activity in the animal in the absence of the agent, is indicative that the agent inhibits human SLP-76 in vivo.

7. The animals of the invention can also used to create additional animals having multiple mutations. In one embodiment, an animal of the invention is bred with an animal carrying another null mutation(s) to create double (or triple, etc.) knockout animals. In another embodiment, an animal of the invention is used to create an embryonic stem cell line into which targeting vectors for functional disruption of additional genes can be introduced. In such a manner, animals having multiple deficiencies in molecules involved in signal transduction can be created, to assess the roles of these molecules in signal transduction.

The SLP-76 knockout animals also can be bred with other knockout or transgenic animals to examine the role of the deficient gene products in various disease conditions. Non-limiting examples of knockout and transgenic animals known in the art (and their disease susceptibilities) which can be bred with the animals of the invention to examine disease states include: interleukin-2 (IL-2) knockout (inflammatory bowel disease)(Sadlack, B. et al. (1993) *Cell* 75:253–261), T cell receptor knockouts (inflammatory bowel disease)(Mombaerts, P. et al. (1993) *Cell* 75:275–282), Major Histocompatibility Complex (MHC) Class II knockout (inflammatory bowel disease) (Mombaerts, P. et al. (1993) *Cell* 75:275–282), interleukin 10 (IL-10) knockout (inflammatory bowel disease)(Kuhn, R. et al. (1993) *Cell* 75:263–274), TGFβ1 knockout (multi-organ inflammation)(Shull, M. M. et al. (1992) *Nature* 359:693–699), TNFα transgenic (arthritis) (Keffer, J. et al. (1991) *EMBO J.* 10:4025–4031) and TNFα transgenic-T cell specific (systemic toxicity of TNFα) (Probert, L. et al. (1993) *J. Immunol.* 151:1894–1906). A disease condition can be induced spontaneously or experimentally in the double (triple, etc.) knockout or transgenic animals to assess the involvement of the affected gene products in the disease.

For the foregoing disease models, it may be preferable to use a SLP-76 deficient animal in which the SLP-76 deficiency can be induced in a conditional manner (e.g., by Cre/Lox recombination or by tetracycline-regulated conditional knockout, as described above), to more accurately approximate the effect of administering a SLP-76 inhibitor to a patient suffering from the disease whose immune system has developed in the presence of SLP-76.

8. The animals of the invention can also be used as recipients of tissue transplants to examine the effect of inhibiting SLP-76 on graft rejection. It may be preferable to use a SLP-76 deficient animal in which the SLP-76 deficiency can be induced in a conditional manner (e.g., by Cre/Lox recombination or by tetracycline-regulated conditional knockout, as described above), to more accurately approximate the effect of administering a SLP-76 inhibitor to a graft recipient whose immune system has developed in the presence of SLP-76.

This invention is further illustrated by the following examples which should not be construed as limiting. The contents of all articles, published patents and patent applications cited throughout the application are hereby incorporated by reference.

EXAMPLE 1

Genomic Cloning of Murine SLP-76 Gene and Generation of SLP-76 Gene Targeting Vector To obtain the initial murine SLP-76 genomic clone for use in constructing a gene targeting vector, a λFIXII library (Stratagene) was screened using standard hybridization techniques with a 330 bp fragment of the mouse SLP-76 cDNA (the cloning of which cDNA is disclosed in Jackman, J. K, et al. (1995) *J. Biol. Chem.* 270:7029–7032. A single 12 kb clone was obtained and subcloned into the NotI site of pBluescript (Stratagene). Sequence analysis using oligomer primers specific for the SLP-76 cDNA sequence revealed the presence of two exons encoding the region from base pairs (bp) 813 to 964 in the SLP-76 cDNA. However, no additional upstream exons were detected in this clone. Subsequent screening of the same genomic library with a more upstream SLP-76 cDNA probe failed to identify additional SLP-76 genomic sequence. Thus, a single pair of polymerase chain reaction (PCR) primers were designed based on the exonic and intronic sequence revealed during the first screen described above. These primers were used in a commercial P1 murine genomic library (strain 129/SVJ) PCR based screening service (Genome Systems, Inc.).

Three independent P1 genomic clones (85–100 kb each) were obtained which contained sequence amplified by the PCR primers. Southern blot analysis revealed the presence of 5' SLP-76 genomic sequence in one of these P1 clones, which was then used for subsequent analysis.

The P1 SLP-76 genomic clone was digested with BamHI, EcoRI, and XbaI as well as various combinations of these enzymes and subjected to Southern blot analysis using various SLP-76 specific cDNA probes. The single digests were also "shotgun" subcloned into the pZero vector (InVitrogen) and introduced into competent DH5α bacteria using a standard chemical transformation protocol. Resultant colonies were screened for SLP-76 specific genomic inserts and plasmid DNA was prepared from positive colonies. Three independent pZero clones containing a 13 kb BamHI fragment, an 8 kb XbaI fragment, and a 5 kb EcoRI fragment were obtained. A partial genomic map of the murine genomic SLP-76 locus is shown in FIG. 1A. This map was generated from restriction digest and Southern blot analysis of both the initial P1 clone as well as the pZero clones. The location of intron/exon boundaries was determined via partial sequence analysis of the pZero clones and each contains characteristic splice junction sequences. The location of exons within a given pZero clone was determined via Southern blotting with labelled oligomers and PCR analysis using a universal primer (T7 or M13reverse) anchored within the pZero parental vector and a primer specific for exonic sequence.

To generate a targeting vector specific for the SLP-76 genomic locus, a 1.6 kb genomic fragment comprised of the genomic sequence immediately upstream of the SLP-76 translational start site was generated by PCR using primers which introduced an EcoRI site at the 5' end of the product and a BamHI restriction site at the 3' end of the amplified product. This PCR fragment was purified and subcloned directly into the appropriate restriction sites in the pPNT parental vector. Next, a 3 kb PCR amplified product flanked by XhoI restriction sites and composed of SLP-76 intronic sequence found between exon 1 and exon 2 was generated and subcloned into the XhoI site of pPNT. Proper orientation of both recombination fragments was confirmed with restriction digest and/or PCR analysis. The resultant targeting vector and a properly recombined mutant allele are also shown in FIG. 1A. Upon specific homologous recombination at the SLP-76 allele, the majority of the first SLP-76 coding exon, including the translational start site, is replaced with a neomycin resistance cassette in opposite transcriptional orientation (also illustrated in FIG. 1A). Both the neomycin and thymidine kinase cassettes contain an independent PGK promoter, allowing for efficient expression regardless of orientation. A properly targeted SLP-76 allele excludes the gene encoding thymidine kinase while a random integration results in the retention of this gene. Thus, homologous recombination at the SLP-76 allele can be identified based on positive selection with G418 and negative selection with gancyclovir.

EXAMPLE 2

Transfection of Embryonic Stem Cells and Generation of Heterozygous and Homozygous SLP-76 Deficient Mice Approximately $2 \times 10^7$ R1 embryonic stem (ES) cells (a gift from Dr. Andras Nagy; R1 ES cells are described further in Nagy, A. et al. (1993) *Proc. Natl. Acad. Sci. USA* 90:8424–8428) were subjected to electroporation with 25 µg of linearized SLP-76 targeting vector using a Bio-Rad gene pulser (240 volts, 500 µFarads). Following 24 hours of culture, G418 (300 µg/ml) and gancyclovir (2 µM) were added to the cultures to select for the presence of the neomycin resistance cassette and the thymidine kinase cassette, respectively. After approximately 10 days of culture in selective media, surviving colonies were isolated and passaged in clonal fashion. Genomic DNA was then isolated from one half of the culture and the remaining cells were frozen. To detect correctly targeted embryonic stem cell clones, Southern blot analysis was performed using genomic DNA samples digested with BamHI. Of 85 neomycin and gancyclovir resistant clones isolated, 6 (7.0%) were found to contain a properly targeted SLP-76 allele. Southern blotting using XbaI digests was used confirm the genotype of the six clones identified.

Figure 1B:
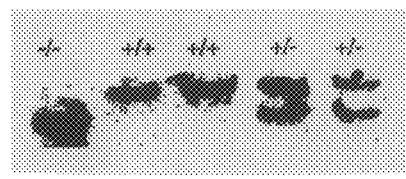

Once the karyotype of several properly targeted ES cell clones had been determined to be normal, these clones (D71 and D28) were microinjected into blastocysts obtained from C57/BL6 mice. The microinjected blastocysts were then transferred to pseudopregnant CD-1 recipient mice. Chimeric offspring were mated with wild type C57/B6 mice and heterozygous offspring were identified by Southern blotting tail genomic DNA. Heterozgous mice were then crossed and wild type, heterozygous, and homozygous SLP-76 deficient mice were identified by Southern blotting. A representative Southern blot is shown in FIG. 1B, which depicts genomic DNA from a homozygous SLP-76 deficient mouse (lane 1), genomic DNA from wild type mice (lanes 2 and 3) and genomic DNA from a heterozygous SLP-76 deficient mice (lanes 4 and 5).

EXAMPLE 3

Characterization of SLP-76 Deficient Mice

Figure 2:
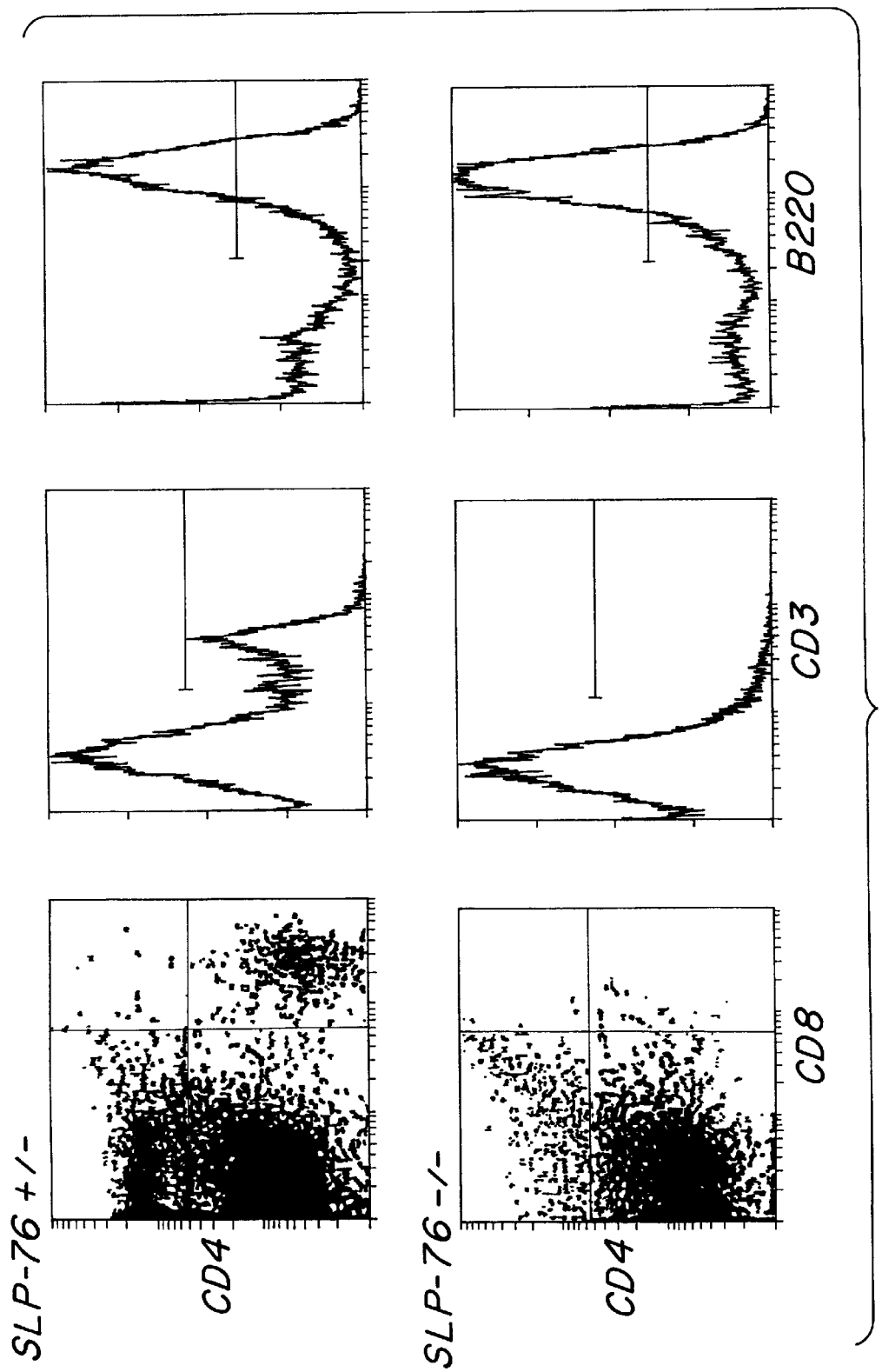
FIG. 2 shows the results of flow cytometry experiments in which peripheral blood cells from either heterozygous (+/−) (top panels) or homozygous (−/−) (bottom panels) SLP-76 deficient mice were stained with CD4 and CD8 (left panels), CD3 (middle panels) or B220 (right panels).

To characterize hematopoietic development and T cell maturation in the SLP-76 deficient mice, flow cytometry experiments were performed with peripheral blood cells, spleen cells and thymic cells from homozygous (−/−) SLP-76 deficient mice. Cells from heterozygous (+/−) mice were used as controls. FIG. 2 shows the results of flow cytometry experiments in which peripheral blood cells from either heterozygous (+/−) (top panels) or homozygous (−/−) (bottom panels) mice were stained with CD4 and CD8 (left panels), CD3 (middle panels) or B220 (right panels). The results revealed a profound block in T cell development as evidenced by the lack of CD3, CD4 or CD8 expressing T cells in the periphery. In contrast, the percentage of B cells in peripheral blood, as determined by the number of B220 expressing cells, was normal. Similar results were observed for spleen cells. Additionally, a normal percentage of macrophages was observed in both peripheral blood and spleen.

Figure 3:
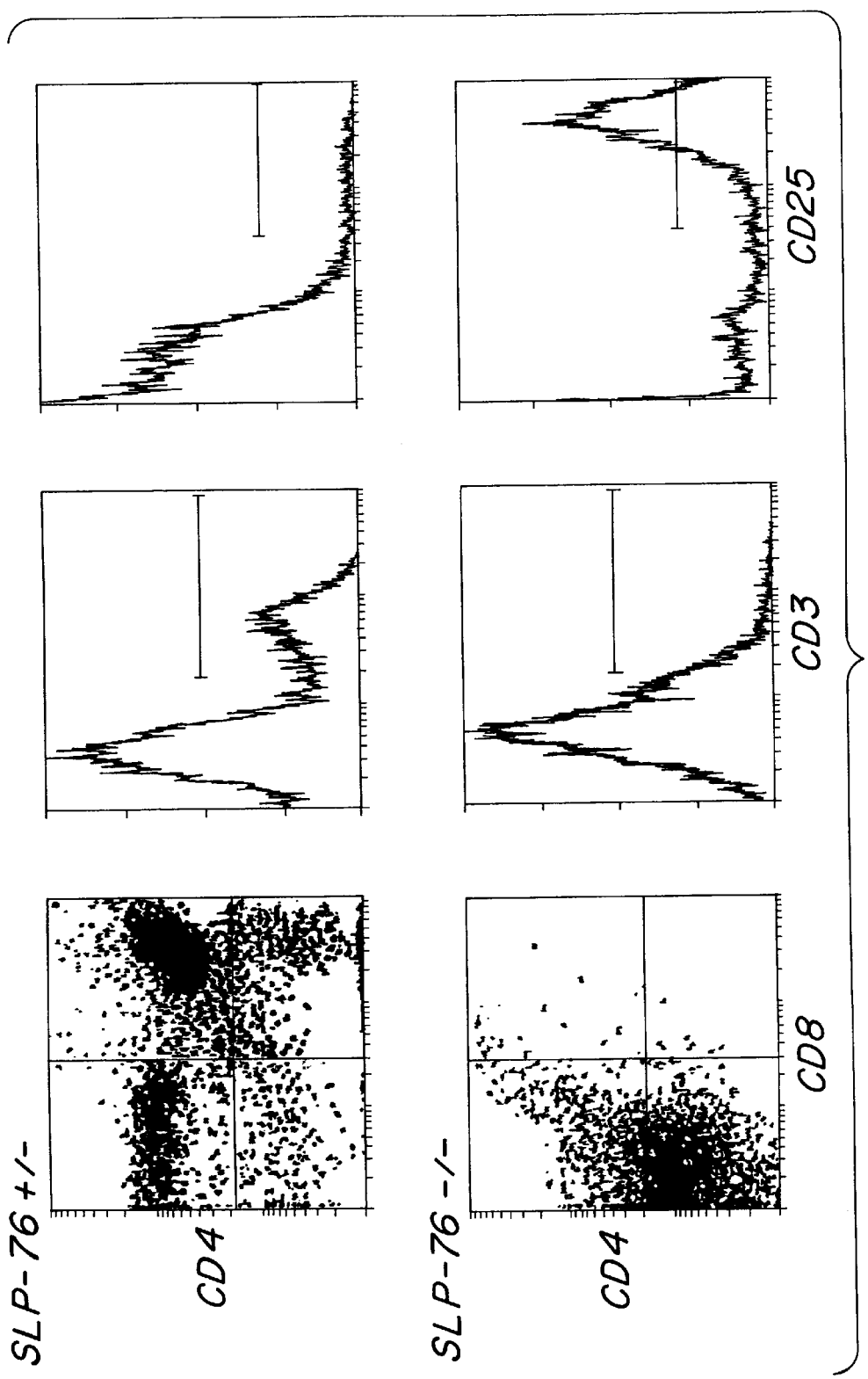
FIG. 3 shows the results of flow cytometry experiments in which thymocytes from either heterozygous (+/−) (top panels) or homozygous (−/−) (bottom panels) SLP-76 deficient mice were stained with CD4 and CD8 (left panels), CD3 (middle panels) or CD25 (right panels).

To further analyze T cell maturation, similar experiments were performed with thymocytes. FIG. 3 shows the results of flow cytometry experiments in which thymocytes from either heterozygous (+/−) (top panels) or homozygous (−/−) (bottom panels) mice were stained with CD4 and CD8 (left panels), CD3 (middle panels) or CD25 (right panels). Thymocytes from −/−mice showed a profound lack of CD4+, CD8+, CD4+ CD8+ and CD3+ cells, as well as an increased population of CD25+ cells, as compared to +/−mice, further evidencing that SLP-76 disruption causes a block in T cell development. Moreover, the homozygous mice also have a much smaller thymus which yields approximately 100-fold fewer thymocytes compared to heterozygous or wild type littermate controls.

The foregoing experiments indicate that SLP-76 is required for normal T cell maturation and that functional disruption of the SLP-76 gene results in a block in T cell development such that SLP-76 deficient animals are severely lacking in peripheral T cells. In contrast, B cell development is not substantially affected, if at all, by functional disruption of the SLP-76 gene. Moreover, while macrophages normally express a significant level of SLP-76, this molecule is not required for macrophage development.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A transgenic mouse whose genome comprises a homozygous engineered disruption in the endogenous SLP-76 gene, wherein the disruption is caused by the insertion of a heterologous DNA sequence, wherein the mouse exhibits a) a percentage of mature peripheral T cells which is substantially decreased as compared to a wild-type mouse and b) a percentage of mature peripheral B-cells and macrophages which is substantially normal as compared to wild-type mouse.

2. The transgenic mouse of claim 1, wherein the heterologous DNA sequence comprises a DNA sequence encoding a selectable marker.

3. The transgenic mouse of claim 2, wherein the selectable marker is neomycin phosphotransferase.

* * * * *

UNITED STATES PATENT AND TRADEMARK OFFICE
CERTIFICATE OF CORRECTION

PATENT NO. : 6,194,633 B1
DATED : February 27, 2001
INVENTOR(S) : Gary Koretzky

It is certified that error appears in the above-identified patent and that said Letters Patent is hereby corrected as shown below:

Column 2,
Line 53, replace "The animals also can also be" with -- The animals also can be --

Column 7,
Line 24, replace "preferably are least several" with -- preferably are at least several --

Column 8,
Line 46, replace "of an mouse SLP-76" with -- of a mouse SLP-76 --

Column 9,
Line 28, replace "see e.g., TERiele H." with -- see e.g., Teriele H. --

Column 10,
Line 38, replace "25:2543-2545;" with -- 25:2543-2545 --

Column 13,
Line 46, replace "can also used to" with -- can also be used to --

Column 14,
Line 60, please continue the paragraph after "Systems, Inc.)." with -- Three independent --

Column 16,
Line 16, replace "DNA Heterozgous mice" with -- DNA Heterozygous mice --

Signed and Sealed this

Eighth Day of October, 2002

*Attest:*

JAMES E. ROGAN
*Attesting Officer*     *Director of the United States Patent and Trademark Office*